(12) United States Patent
Hagihara et al.

(10) Patent No.: US 7,759,491 B2
(45) Date of Patent: Jul. 20, 2010

(54) METHOD FOR PRODUCING INDAZOL-3-YLMETHYL PHOSPHONIUM SALT

(75) Inventors: Koji Hagihara, Chicago, IL (US); Tsutomu Matsumura, Sakai (JP); Masahiro Hoshikawa, Sakai (JP); Iwao Chujo, Kaizuka (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 339 days.

(21) Appl. No.: 11/912,355

(22) PCT Filed: Apr. 28, 2006

(86) PCT No.: PCT/JP2006/309001
§ 371 (c)(1),
(2), (4) Date: Oct. 23, 2007

(87) PCT Pub. No.: WO2006/118257
PCT Pub. Date: Nov. 9, 2006

(65) Prior Publication Data
US 2009/0069568 A1 Mar. 12, 2009

(30) Foreign Application Priority Data
Apr. 28, 2005 (JP) .............................. 2005-130705

(51) Int. Cl.
*C07F 9/645* (2006.01)
(52) U.S. Cl. .................................................... 548/113
(58) Field of Classification Search .................. 548/113
See application file for complete search history.

(56) References Cited
FOREIGN PATENT DOCUMENTS
WO 20040050088 6/2004

OTHER PUBLICATIONS
Rawal et al, J. Org. Chem., vol, 52, No. 1, 1987.*
* cited by examiner

*Primary Examiner*—Kamal A Saeed
(74) *Attorney, Agent, or Firm*—Fitzpatrick, Cella, Harper & Scinto

(57) ABSTRACT

The present invention provides a method for producing an indazol-3-ylmethyl phosphonium salt represented by Formula (IV):

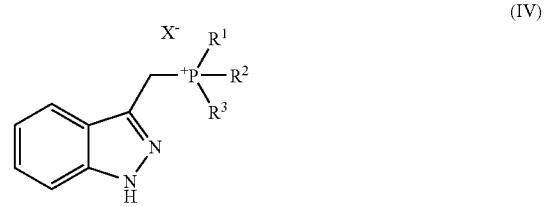

(IV)

[wherein X represents halogen, $OSO_2R^a$ (wherein $R^a$ represents substituted or unsubstituted lower alkyl, substituted or unsubstituted aryl or the like), or $OC(=O)R^b$ (wherein $R^b$ has the same meaning as the above $R^a$), or the like, and $R^1$, $R^2$ and $R^3$ may be the same or different and each represents substituted or unsubstituted aryl or the like] or a salt thereof, which comprises reacting a compound represented by Formula (I):

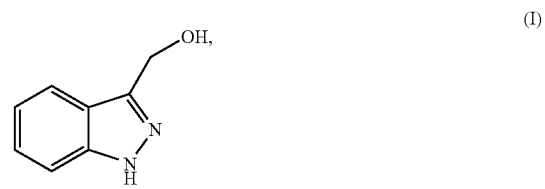

(I)

a compound represented by Formula (II):

H—X  (II)

(wherein X has the same meaning as defined above), and a compound represented by Formula (III):

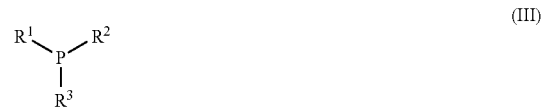

(III)

(wherein $R^1$, $R^2$ and $R^3$ have the same meanings as defined above, respectively), and the like.

11 Claims, No Drawings

METHOD FOR PRODUCING INDAZOL-3-YLMETHYL PHOSPHONIUM SALT

TECHNICAL FIELD

The present invention relates to a method for producing an indazol-3-ylmethyl phosphonium salt or a salt thereof useful as a synthetic intermediate of an indazole derivative having anti-tumor activity, protein kinase inhibitory activity or the like, etc.

BACKGROUND ART

An indazol-3-ylmethyl triphenyl phosphonium salt [Compound (IVb)] represented by Formula (IVb):

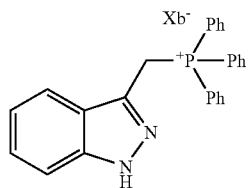

(wherein Ph represents phenyl, $X^b$ represents each atom of chlorine, bromine, or iodine) is known as useful synthetic intermediate of indazole derivative which is useful as an anti-tumor agent or a protein kinase inhibitor (refer to Patent Document 1 and Patent Document 2).

According to the said gazettes, Compound (IVb) can be produced from commercially available indazol-3-carboxylic acid by 4 steps in a similar manner to methods described in Nonpatent Document 1 or Nonpatent Document 2. However, these methods require number of steps and ate not suitable for industrial mass production. Therefore, simpler and more efficient producing method of indazol-3-ylmethyl phosphonium salt is desired.

Patent Document 1: WO2005/012257
Patent Document 2: WO2005/012258
Nonpatent Document 1: Journal of Organic Chemistry, 1987, vol. 52, p. 19
Nonpatent Document 2: Canadian Journal of Chemistry, 1973, vol. 51, p. 792

DISCLOSURE OF THE INVENTION

Problems to be Solved by the Invention

An object of the present invention is to provide a method for producing an indazol-3-ylmethyl phosphonium salt or a salt thereof useful as a synthetic intermediate of an indazole derivative having anti-tumor activity, protein kinase inhibitory activity or the like, etc.

Means for Solving the Problems

The present invention relates to the following (1) to (15).
(1) A method for producing an indazol-3-ylmethyl phosphonium salt represented by Formula (IV):

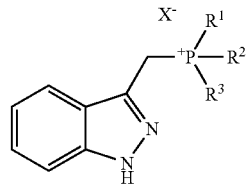

[wherein, X represents halogen, $ONO_2$, $OSO_3H$, $OSO_2R^a$ (wherein $R^a$ represents substituted or unsubstituted lower alkyl, substituted or unsubstituted aryl, or a substituted or unsubstituted aromatic heterocyclic group), or $OC(=O)R^b$ (wherein $R^b$ has the same meaning as the above $R^a$), and $R^1$, $R^2$ and $R^3$ may be the same or different and each represents substituted or unsubstituted aryl or a substituted or unsubstituted aromatic heterocyclic group] or a salt thereof, which comprises reacting a compound represented by Formula (I):

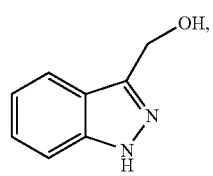

a compound represented by Formula (II):

(wherein X has the same meaning as defined above), and a compound represented by Formula (III):

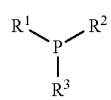

(wherein $R^1$, $R^2$ and $R^3$ have the same meanings as defined above, respectively).

(2) The method for producing an indazol-3-ylmethyl phosphonium salt or a salt thereof according to the above (1), wherein $R^1$, $R^2$ and $R^3$ may be the same or different and each represents substituted or unsubstituted aryl.

(3) The method for producing an indazol-3-ylmethyl phosphoniumsalt or a salt thereof according to the above (1), wherein $R^1$, $R^2$ or $R^3$ is phenyl.

(4) The method for producing an indazol-3-ylmethyl phosphoniumsalt or a salt thereof according to any of the above (1) to (3), wherein X is halogen.

(5) The method for producing an indazol-3-ylmethyl phosphonium salt or a salt thereof according to any of the above (1) to (3), wherein X is $ONO_2$, $OSO_3H$, $OSO_2R^a$ (wherein $R^a$ has the same meaning as defined above), or $OC(=O)R^b$ (wherein $R^b$ has the same meaning as defined above).

(6) The method for producing an indazol-3-ylmethyl phosphonium salt or a salt thereof according to any of the above (1) to (3), wherein X is $OSO_2R^a$ (wherein $R^a$ has the same meaning as defined above).

(7) The method for producing an indazol-3-ylmethyl phosphonium salt or a salt thereof according to any of the above (1) to (3), wherein X is OC(=O)$R^b$ (wherein $R^b$ has the same meaning as defined above).

(8) A method for producing an indazole derivative represented by Formula (V):

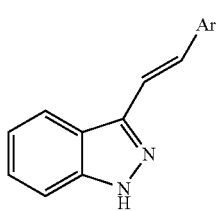

(wherein, Ar represents substituted or unsubstituted aryl, or a substituted or unsubstituted heterocyclic group) or a salt thereof, which comprises a step of reacting a compound represented by Formula (I):

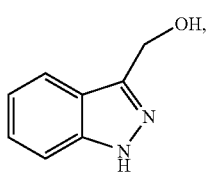

a compound represented by Formula (II):

(wherein X has the same meaning as defined above), and a compound represented by Formula (III):

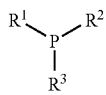

(wherein $R^1$, $R^2$ and $R^3$ have the same meanings as defined above, respectively) to obtain indazol-3-ylmethyl phosphonium salt represented by Formula (IV):

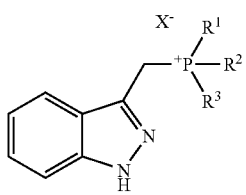

(wherein X, $R^1$, $R^2$ and $R^3$ have the same meanings as defined above, respectively) or a salt thereof.

(9) The method for producing an indazole derivative or a salt thereof according to the above (8), wherein Ar is substituted or unsubstituted aryl.

(10) The method for producing an indazole derivative or a salt thereof according to the above (8), wherein Ar is substituted or unsubstituted phenyl.

(11) The method for producing an indazole derivative or a salt thereof according to the above (8), wherein Ar is a substituted or unsubstituted aromatic heterocyclic group.

(12) An indazol-3-ylmethyl phosphonium salt represented by Formula (IVa):

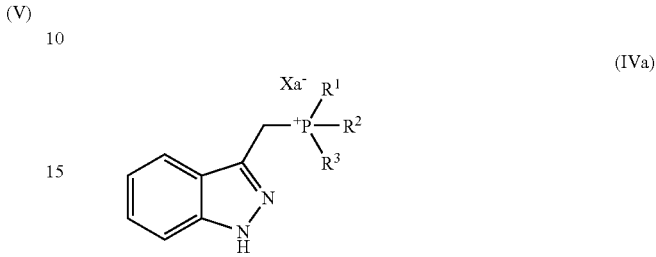

[wherein $R^1$, $R^2$ or $R^3$ have the same meanings as defined above, respectively, and Xa represents $ONO_2$, $OSO_3H$, $OSO_2R^a$ (wherein $R^a$ has the same meaning as defined above), or OC(=O)$R^b$ (wherein $R^b$ has the same meaning as defined above)] or a salt thereof.

(13) The indazol-3-ylmethyl phosphonium salt or the salt thereof according to the above (12), wherein $R^1$, $R^2$ and $R^3$ may be the same or different and each represents substituted or unsubstituted aryl.

(14) The indazol-3-ylmethyl phosphonium salt or the salt thereof according to the above (12), wherein $R^1$, $R^2$ and $R^3$ are phenyl.

(15) The indazol-3-ylmethyl phosphonium salt or the salt thereof according to the above (12), wherein Xa is $OSO_2R^a$ (wherein $R^a$ has the same meaning as defined above), or OC(=O)$R^b$ (wherein $R^b$ has the same meaning as defined above).

Effect of the Invention

The present invention provides a method for producing an indazol-3-ylmethyl phosphonium salt or a salt thereof useful as a synthetic intermediate of an indazole derivative having anti-tumor activity, protein kinase inhibitory activity or the like, etc.

BEST MODE FOR CARRYING OUT THE INVENTION

Hereinafter, the compounds represented by Formulae (I), (II), (III), (IV), (IVa) and (V) are referred to as Compounds (I), (II), (III), (IV), (IVa) and (V), respectively, and the same applies to compounds of other formula numbers.

In the definitions of respective groups in Formulae (II), (III), (IV) and (IVa):

Examples of the lower alkyl include straight-chain or branched alkyl groups having 1 to 10 carbon atoms, such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, isooctyl, nonyl, and decyl.

Examples of the aryl include monocyclic, bicyclic or tricyclic aryl groups having 6 to 14 carbon atoms, such as phenyl, naphthyl, indenyl, and anthranil.

Examples of the aromatic heterocyclic groups include 5- or 6-membered monocyclic aromatic heterocyclic groups containing at least one atom selected from a nitrogen atom, an oxygen atom and a sulfur atom, and bicyclic or tricyclic condensed aromatic heterocyclic groups containing at least one atom selected from a nitrogen atom, an oxygen atom and a sulfur atom in which 3- to 8-membered rings are condensed, such as pyridyl, pyrazinyl, pyrimidinyl, pyridazinyl, benzimidazolyl, 2-oxobenzimidazolyl, benzotriazolyl, benzofuryl, benzothienyl, purinyl, benzoxazolyl, benzothiazolyl, benzodioxolyl, indazolyl, indolyl, isoindolyl, purinyl, quinolyl, isoquinolyl, phthalazinyl, naphthyridinyl, quinoxalinyl, pyrrolyl, pyrazolyl, quinazolinyl, cinnolinyl, triazolyl, tetrazolyl, imidazolyl, oxazolyl, isooxazolyl, thiazolyl, isothiazolyl, thienyl, and furyl.

The halogen represents each atoms of fluorine, chlorine, bromine and iodine.

Examples of the substituents in the substituted lower alkyl include 1 to 10 substituents which may be the same or different, such as halogen, lower alkoxy, aryl, and an aromatic heterocyclic group. Here, halogen, aryl, and an aromatic heterocyclic group have the same meanings as defined above, respectively and lower alkyl moiety of the lower alkoxy has the same meaning as the above lower alkyl.

Examples of substituents in the substituted aryl and substituted aromatic heterocyclic group include 1 to 10 substituents which may be the same or different, such as halogen, hydroxy, cyano, mono- or di-(substituted or unsubstituted lower alkyl)amino [examples of the substituents of the substituted lower alkylamino or di-(substituted lower alkyl) amino include 1 to 3 substituents which may be the same or different, such as halogen, amino, hydroxy, and lower alkoxy], nitro, carboxy, sulfo, lower alkyl, lower alkoxy and the like. Here, halogen and lower alkyl have the same meanings as defined above, respectively and the lower alkyl moieties of the lower alkoxy and the mono- or di-lower alkylamino have the same meaning as the above lower alkyl. Two lower alkyl moieties of the di-lower alkylamino may be the same or different.

In the definitions of respective groups in Formula (V), aryl has the same meaning as defined above.

Examples of the heterocyclic groups include aromatic heterocyclic group, aliphatic heterocyclic group and the like.

The aromatic heterocyclic group has the same meaning as defined above.

Examples of the aliphatic heterocyclic groups include monocyclic aliphatic heterocyclic groups containing at least one atom selected from a nitrogen atom, a sulfur atom, and an oxygen atom, and condensed aliphatic heterocyclic groups in which two or more rings are condensed such as pyrrolidinyl, 2,5-dioxopyrrolidinyl, thiazolidinyl, oxazolidinyl, piperidyl, 1,2-dihydropyridyl, piperazinyl, homopiperazinyl, morpholinyl, thiomorpholinyl, pyrazolinyl, oxazolinyl, dioxolanyl, tetrahydropyranyl, tetrahydrothiopyranyl, tetrahydrofuryl, tetrahydroquinolyl, tetrahydroisoquinolyl, tetrahydroquinoxalinyl, octahydroquinolyl, dihydroindolyl, and 1,3-dioxoisoindolyl.

Examples of substituents in the substituted aryl, substituted phenyl, and substituted heterocyclic group include 1 to 3 substituents which may be the same or different, such as halogen, nitro, nitroso, carboxy, heteroaroyl, substituted or unsubstituted lower alkyl, substituted or unsubstituted cycloalkyl, substituted or unsubstituted lower alkenyl, substituted or unsubstituted lower alkynyl, substituted or unsubstituted lower alkoxycarbonyl, substituted or unsubstituted lower alkanoyl, substituted or unsubstituted cycloalkylcarbonyl, substituted or unsubstituted aryl [examples of the substituents in the substituted aryl include 1 to 3 substituents such as halogen, hydroxy, nitro, cyano, carboxy, lower alkanoyl, lower alkoxycarbonyl, aralkyl, aroyl, substituted or unsubstituted lower alkyl (the substituents in the substituted lower alkyl include 1 to 3 substituents such as hydroxy), and substituted or unsubstituted lower alkoxy (the substituents in the substituted lower alkoxy include 1 to 3 substituents such as hydroxy)], substituted or unsubstituted alicyclic heterocyclic carbonyl (the substituents in the substituted alicyclic heterocyclic carbonyl include 1 to 3 substituents such as halogen, hydroxy, oxo, lower alkyl, and lower alkoxy), $NR^{4a}R^{4b}$ {wherein $R^{4a}$ or $R^{4b}$ may be the same or different, and each represents a hydrogen atom, lower alkylsulfonyl, substituted or unsubstituted lower alkyl, substituted or unsubstituted cycloalkyl, substituted or unsubstituted lower alkenyl, substituted or unsubstituted lower alkynyl, substituted or unsubstituted lower alkoxy, substituted or unsubstituted lower alkanoyl, substituted or unsubstituted cycloalkylcarbonyl, substituted or unsubstituted aryl [the substituents in the substituted aryl include 1 to 3 substituents such as halogen, hydroxy, nitro, cyano, carboxy, lower alkanoyl, lower alkoxycarbonyl, aralkyl, aroyl, substituted or unsubstituted lower alkyl (the substituents in the substituted lower alkyl include 1 to 3 substituents such as hydroxy), substituted or unsubstituted lower alkoxy, (the substituents in the substituted lower alkoxy include 1 to 3 substituents such as hydroxy)], substituted or unsubstituted aroyl [the substituents in the substituted aroyl include 1 to 3 substituents such as halogen, hydroxy, nitro, cyano, carboxy, lower alkanoyl, lower alkoxycarbonyl, aralkyl, aroyl, substituted or unsubstituted lower alkyl (the substituents in the substituted lower alkyl include 1 to 3 substituents such as hydroxy), substituted or unsubstituted lower alkoxy (the substituents in the substituted lower alkoxy include 1 to 3 substituents such as hydroxy), and the like] or a substituted or unsubstituted heterocyclic group [the substituents in the substituted heterocyclic group include 1 to 3 substituents such as halogen, hydroxy, nitro, cyano, carboxy, lower alkanoyl, lower alkoxycarbonyl, aralkyl, aroyl, substituted or unsubstituted lower alkyl (the substituents in the substituted lower alkyl include 1 to 3 substituents such as hydroxy), substituted or unsubstituted lower alkoxy (the substituents in the substituted lower alkoxy include 1 to 3 substituents such as hydroxy), and the like], or $R^{4a}$ or $R^{4b}$ are combined together with the adjacent nitrogen atom thereto to form a substituted or unsubstituted heterocyclic group [the substituents in the substituted heterocyclic group formed together with the adjacent nitrogen atom thereto include 1 to 3 substituents such as halogen, amino, nitro, hydroxy, oxo, cyano, carboxy, lower alkoxycarbonyl, aralkyl, aroyl, heteroaroyl, substituted or unsubstituted lower alkyl (the substituents in the substituted lower alkyl include 1 to 3 substituents such as hydroxy or lower alkoxy), substituted or unsubstituted lower alkoxy (the substituents in the substituted lower alkoxy include 1 to 3 substituents such as hydroxy, or lower alkoxy), substituted or unsubstituted lower alkanoyl (the substituents in the substituted lower alkanoyl include 1 to 3 substituents such as amino, hydroxy, lower alkoxy, lower alkanoylamino, or N-lower alkanoyl-N-lower alkylamino), substituted or unsubstituted alicyclic heterocyclic carbonyl (the substituents in the substituted alicyclic heterocyclic carbonyl include 1 to 3 substituents such as halogen, hydroxy, oxo, lower alkyl, or lower alkoxy) and the like]}, $CONR^{4c}R^{4d}$ (wherein $R^{4c}$ and $R^{4d}$ have the same meanings as the above $R^{4a}$ and $R^{4b}$, respectively), $OR^5$ {wherein $R^5$ represents a hydrogen atom, substituted or unsubstituted lower alkyl, substituted or unsubstituted cycloalkyl, substituted or unsubstituted aryl [the substituents in the substituted aryl include 1 to 3 substituents such as halogen, hydroxy, nitro cyano, carboxy, lower alkanoyl, lower alkoxycarbonyl, aralkyl, aroyl, substituted or unsubstituted lower alkyl (the substituents in the substituted lower alkyl include 1 to 3 substituents such as hydroxy), substituted or unsubstituted lower alkoxy (the substituents in the substituted lower alkoxy include 1 to 3 substituents such as hydroxy), and the like] or a substituted or unsubstituted heterocyclic group [the substituents in the substituted heterocyclic group include 1 to 3 substituents such as halogen, hydroxy, nitro, cyano, carboxy, lower alkanoyl, lower alkoxycarbonyl, aralkyl, aroyl, substituted or unsubstituted lower alkyl (the substituents in the substituted lower alkyl include 1 to 3 substituents such as hydroxy), substituted or unsubstituted lower alkoxy (the substituents in the substituted lower alkoxy include 1 to 3 substituents such as hydroxy), and the like], and the like}. Also, examples of substituents in the substituted heterocyclic group may be, in addition to the above, oxo or —O($CR^{6a}R^{6b}$)$_n$O— (wherein $R^{6a}$ and $R^{6b}$ may be the same or different and each represents a hydrogen atom or lower alkyl, n represents 2 or 3, and two oxygen atoms of terminus are combined to same carbon atoms of a substituted heterocyclic group).

In the definitions of substituents in substituted aryl or a substituted heterocyclic group, halogen, lower alkyl, aryl or a heterocyclic group have the same meanings as defined above, respectively, or lower alkyl moieties of lower alkoxy, lower alkoxycarbonyl, N-lower alkanoyl-N-lower alkylamino or lower alkylsulfonyl have the same meaning as the above lower alkyl, alkylene moieties of the aralkyl have the same meaning as the group produced by removing one hydrogen atom from the above lower alkyl, aryl moieties of aralkyl or aroyl have the same meaning as the above aryl, aromatic heterocyclic moieties of heteroaroyl have the same meaning as the above aromatic heterocyclic group, alicyclic heterocyclic moieties of alicyclic heterocyclic carbonyl have the same meaning as the above alicyclic heterocyclic group.

Examples of the cycloalkyl moieties of the cycloalkyl or cycloalkylcarbonyl include cycloalkyl having 1 to 10 carbon atoms, such as cyclopropyl, cyclobutyl, cyclopentyl, cyclohexyl, cycloheptyl, cyclooctyl, cyclodecyl, noradamantyl, adamantyl, bicyclo[2.2.1]heptyl, bicyclo[2.2.2]octyl, bicyclo[3.3.0]octyl, and bicyclo[3.3.1]nonyl.

Examples of the lower alkenyl include straight-chain or branched alkenyl groups having 2 to 10 carbon atoms, such as vinyl, allyl, 1-propenyl, 1-butenyl, 3-butenyl, 2-pentenyl, 4-pentenyl, 2-hexenyl, 5-hexenyl, 2-decenyl, and 9-decenyl.

Examples of the lower alkynyl include straight-chain or branched alkynyl groups having 2 to 10 carbon atoms, such as ethynyl, 2-propynyl, 3-butynyl, 4-pentynyl, 5-hexynyl, and 9-decynyl.

Examples of the lower alkanoyl moieties of the lower alkanoyl, lower alkanoylamino, or N-lower alkanoyl-N-lower alkylamino include straight-chain or branched alkanoyl having 1 to 8 carbon atoms, such as formyl, acetyl, propionyl, butyryl, isobutyryl, valeryl, isovaleryl, pivaloyl, hexanoyl, heptanoyl, and octanoyl.

Examples of the heterocyclic groups formed together with the adjacent nitrogen atom thereto include 5- or 6-membered monocyclic heterocyclic groups containing at least one nitrogen atom (the monocyclic heterocyclic groups may also contain another nitrogen atom, an oxygen atom or a sulfur atom), and bicyclic or tricyclic condensed-ring heterocyclic groups containing at least one nitrogen atom in which 3- to 8-membered rings are condensed (the condensed-ring heterocyclic groups may also contain another nitrogen atom, an oxygen atom or a sulfur atom), such as pyrrolidinyl, piperidino, piperazinyl, morpholino, thiomorpholino, homopiperidino, homopiperazinyl, tetrahydropyridyl, tetrahydroquinolyl, and tetrahydroisoquinolyl.

Examples of substituents in the substituted lower alkyl, substituted cycloalkyl, substituted lower alkenyl, substituted lower alkynyl, substituted lower alkoxy, substituted lower alkoxycarbonyl, substituted lower alkanoyl and substituted cycloalkylcarbonyl include 1 to 3 substituents which may be the same or different, such as hydroxy, oxo, carboxy, lower alkoxy, lower alkoxycarbonyl, lower alkanoylamino, N-(lower alkanoyl)-N-(lower alkyl)amino, heteroaroyl, arylsulfonyl, substituted or unsubstituted aryl (the substituents in the substituted aryl include carboxy, lower alkoxy, lower alkoxycarbonyl and the like), substituted or unsubstituted heterocyclic group (the substituents in the substituted heterocyclic group include carboxy, lower alkoxy, lower alkoxycarbonyl and the like), $CONR^{7a}R^{7b}$ {wherein $R^{7a}$ and $R^{7b}$ may be the same or different and each represents a hydrogen atom, substituted or unsubstituted lower alkyl [the substituents in the substituted lower alkyl include 1 to 3 substituents, such as halogen, hydroxy, oxo, nitro, cyano, carboxy, lower alkanoyl, lower alkoxycarbonyl, aroyl, substituted or unsubstituted lower alkoxy (the substituents in the substituted lower alkoxy include 1 to 3 substituents such as hydroxy), and the like], or substituted or unsubstituted cycloalkyl [the substituents in the substituted cycloalkyl include 1 to 3 substituents such as halogen, hydroxy, oxo, nitro, cyano, carboxy, lower alkanoyl, lower alkoxycarbonyl, aroyl, substituted or unsubstituted lower alkoxy (the substituents in the substituted lower alkoxy include 1 to 3 substituents such as hydroxy), and the like], or $R^{7a}$ and $R^{7b}$ are combined together with the adjacent nitrogen atom thereto to form a substituted or unsubstituted heterocyclic group [the substituents in the substituted heterocyclic group combined together with the adjacent nitrogen atom thereto include 1 to 3 substituents such as halogen, hydroxy, oxo, nitro, cyano, carboxy, lower alkanoyl, lower alkoxycarbonyl, aralkyl, aroyl, substituted or unsubstituted lower alkyl (the substituents in the substituted lower alkyl include 1 to 3 substituents such as hydroxy), substituted or unsubstituted lower alkoxy (the substituents in the substituted lower alkoxy include 1 to 3 substituents such as hydroxy) and the like]}, $NR^{7c}R^{7d}$ (wherein $R^{7c}$ and $R^{7d}$ have the same meanings as the above $R^{7a}$ and $R^{7b}$, respectively) and the like.

Here, halogen, lower alkyl, cycloalkyl, lower alkanoyl, lower alkanoyl moieties of lower alkanoylamino and N-(lower alkanoyl)-N-(lower alkyl)amino, aryl, heterocyclic group, heterocyclic group formed together with the adjacent nitrogen atom thereto each have the same meanings as the above, respectively; lower alkyl moieties of lower alkoxy, lower alkoxycarbonyl, and N-(lower alkanoyl)-N-(lower alkyl)amino have the same meaning as the above lower alkyl; the alkylene moieties of the aralkyl have the same meanings as the group produced by removing one hydrogen atom from the above-described lower alkyl; the aryl moieties of the aralkyl, aroyl or arylsulfonyl have the same meaning as the above aryl; the aromatic heterocyclic moieties of the heteroaroyl have the same meaning as the above aromatic heterocyclic group.

Examples of the salts of Compounds (IV) or (V) include acid addition salts including inorganic acid salts such as hydrochloride, hydrobromide, nitrate, sulfate, and phosphate, organic acid addition salts such as benzenesulfonate, benzoate, citrate, fumarate, gluconate, lactate, maleate, malate, oxalate, methanesulfonate, and tartrate, alkali metal salts such as sodium salt and potassium salt, alkaline earth metal salts such as magnesium salt and calcium salt, metal salts such as aluminum salt, and zinc salt, ammonium salts such as ammonium and tetramethylammonium, organic amine addition salts such as an addition salt of morpholine or piperidine, amino acid addition salts such as an addition salt of glycine, phenylalanine, lysine, aspartic acid or glutamic acid.

Next, the Production Method of Compound (IV) will be exemplified below.

Production Method:

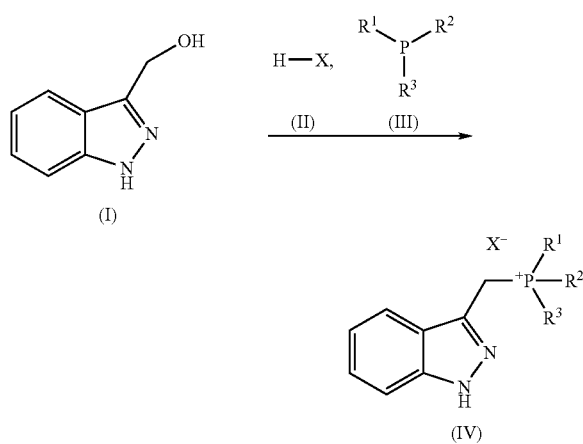

(wherein $R^1$, $R^2$, $R^3$, and X have the same meanings as defined above, respectively)

Compound (IV) can be obtained by reacting Compound (I), Compound (II), and Compound (III) in a solvent or without a solvent.

Examples of the Compound (II) include hydrogen halide such as hydrochloric acid, hydrobromic acid, hydriodic acid, hydrofluoric acid, sulfonic acids such as methanesulfonic acid, trifluoromethanesulfonic acid, benzenesulfonic acid, paratoluenesulfonic acid, carboxylic acids such as acetic acid, propionic acid, trichloroacetic acid, trifluoroacetic acid, benzoic acid, methylbenzoic acid, methoxybenzoic acid, trichlorobenzoic acid, trifluorobenzoic acid, pentafluorobenzoic acid and nicotinic acid, sulfuric acid, nitric acid and the like. To Compound (I), usually 0.5 to 10 equivalents of, preferably 0.9 to 1.5 equivalents of, Compound (II) are used.

Examples of the Compound (III) include triphenylphosphine, tri-p-tolylphosphine, trinaphtylphosphine, tripyridylphosphine, trifurylphosphine and the like. To Compound (I), generally 0.5 to 10 equivalents of, preferably 0.9 to 1.5 equivalents of, Compound (III) are used.

Also, Compound (II) or Compound (III) can be used as a form of salt such as triphenylphosphine hydrobromide.

Examples of the solvents include aliphatic hydrocarbon such as pentane, hexane, heptane, and cyclohexane, aromatic hydrocarbon such as toluene and xylene, halogenated hydrocarbon such as dichloromethane, chloroform, dichloroethane, nonaromatic organic solvents such as acetonitrile, propionitrile, dimethylsulfoxide, N,N-dimethylformamide, N,N-dimethylacetamide, 1-methyl-2-pyrrolidinone, 1,3-dimethyl-2-imidazolidinone, ether such as dioxane, tetrahydrofuran, diethyl ether, cyclopentylmethyl ether, dimetoxyethane, and ethyleneglycoldimethylether, ester such as methyl acetate, ethyl acetate, and isopropyl acetate, alcohol such as methanol, ethanol, n-propanol, and 2-propanol, water and the like. These may be used alone or in a combination. To Compound (II), generally 1 to 100 times (weight) of, preferably 5 to 25 times (weight) of solvent is used.

The reaction is generally carried out at a temperature between −20° C. and the boiling point of the solvent used, preferably a temperature between 40 to 100° C. for 5 minutes to 48 hours.

Compound (I) can be obtained from indazol-3-carboxylic acid according to methods described in WO2003/035644 or U.S. Pat. No. 553246 or methods similar thereto. Compound (II) or (III) can be obtained as commercially available products and used as it is or purified.

Compound (V) can be obtained from Compound (IV) obtained in the Production Method of the present invention, according to methods described in, for example, WO2005/012257 or WO2005/012258.

The desired compounds in the above-described Production Method can be isolated and purified by appropriately combining separation and purification methods conventionally used in synthetic organic chemistry, for example, filtration, extraction, washing, drying, concentration, recrystallization, various kinds of chromatography and the like. Compound (I) can also be subjected to the reactions without purification.

Among Compounds (II), (III), (IV) and (V), there may exist stereoisomers such as geometrical isomers and optical isomers. All possible isomers including these and mixtures thereof are comprised in the present invention.

Further, Compound (IV) or Compound (V) may exist in the form of adducts with water or various solvents, and these adducts can also be comprised in the present invention.

Specific examples of the Compound (IV) obtained in the present invention will be illustrated below in Table 1.

TABLE 1

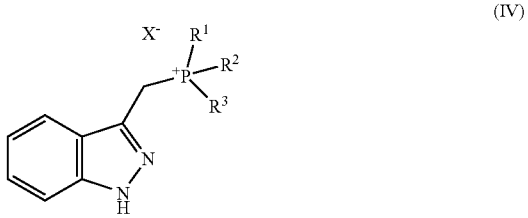

| Compound Number | X | $R^1$ | $R^2$ | $R^3$ |
|---|---|---|---|---|
| 1 | Cl | phenyl | phenyl | phenyl |

TABLE 1-continued (IV)

| Compound Number | X | R¹ | R² | R³ |
|---|---|---|---|---|
| 2 | Br | phenyl | phenyl | phenyl |
| 3 | I | phenyl | phenyl | phenyl |
| 4 | OSO₂CH₃ | phenyl | phenyl | phenyl |
| 5 | OSO₂-C₆H₄-CH₃ | phenyl | phenyl | phenyl |
| 6 | OSO₂CF₃ | phenyl | phenyl | phenyl |
| 7 | O₂CCF₃ | phenyl | phenyl | phenyl |

Certain embodiments of the present invention will be illustrated in the following Examples and Reference Examples. But the present invention is not limited to them.

EXAMPLE 1

Synthesis of [(1H-indazol-3-yl)methyl]triphenylphosphonium chloride (Compound 1)

Compound (I) (1.00 g, 6.75 mmol) obtained in the Reference Example 1 was dissolved in propionitrile (20 mL) and 8.0 mol/L hydrochloric acid (844 μL, 6.75 mmol) and triphenylphosphine (1.77 g, 6.75 mmol) were added thereto under ice-cooling, followed by stirring for 10 hours under heating and reflux. The reaction solution was stirred for 2 hours under ice-cooling. Then, precipitated crystal was collected by filtration and was washed with propionitrile (5 mL). The obtained crystal was dried under reduced pressure to thereby yield Compound 1 (2.33 g, 5.43 mmol, 80%).

$^1$H-NMR (DMSO-$d_6$, ppm) δ 5.67 (2H, d, J=15.2 Hz), 6.97 (1H, t, J=ca. 8 Hz), 7.28 (1H, t, J=ca. 8 Hz), 7.46 (1H, d, J=8.4 Hz), 7.63 (1H, d, J=8.4 Hz), 7.66-7.88 (15H, m), 13.42 (1H, br).

$^{13}$C-NMR (DMSO-$d_6$, ppm) δ 20.9 (d, $J_{C-P}$=51.0 Hz), 110.3, 118.9 (d, $J_{C-P}$=86.4 Hz), 119.7, 120.2, 122.5 (d, $J_{C-P}$=6.2 Hz), 126.3, 129.7 (d, $J_{C-P}$=12.4 Hz), 133.1 (d, $J_{C-P}$=9.3 Hz), 133.9 (d, $J_{C-P}$=10.6 Hz), 134.7 (d, $J_{C-P}$=2.5 Hz), 140.3.

Mass analysis as $C_{26}H_{22}N_2P$, Calculated: 393.1521 [M]⁺, Found: 393.1531 [1.1 mDa].

Melting point: 278-279° C.

EXAMPLE 2

Synthesis of [(1H-indazol-3-yl)methyl]triphenylphosphonium bromide (Compound 2)

Compound (I) (1.00 g, 6.75 mmol) obtained in the Reference Example 1 was dissolved in propionitrile (10 mL) and aqueous solution of 47% hydrobromide (782 μL, 6.75 mmol) and triphenylphosphine (1.77 g, 6.75 mmol) were added thereto under ice-cooling, followed by stirring for 5 hours under heating and reflux. The reaction solution was stirred for 2 hours under ice-cooling. Then, precipitated crystal was collected by filtration and washed with propionitrile (5 mL). The obtained crystal was dried under reduced pressure to thereby yield Compound 2 (2.84 g, 6.00 mmol, 88.8%).

$^1$H-NMR (DMSO-$d_6$, ppm) δ 5.63 (2H, d, J=15.2 Hz), 6.99 (1H, t, J=ca. 8 Hz), 7.30 (1H, t, J=ca. 8 Hz), 7.45 (1H, d, J=8.4 Hz), 7.61 (1H, d, J=8.4 Hz), 7.66-7.88 (15H, m), 13.16 (1H, br).

$^{13}$C-NMR (DMSO-$d_6$, ppm) δ 20.9 (d, $J_{C-P}$=52.8 Hz), 110.2, 118.8 (d, $J_{C-P}$=86.4 Hz), 119.6, 120.3, 122.5 (d, $J_{C-P}$=5.6 Hz), 126.5, 129.8 (d, $J_{C-P}$=12.4 Hz), 133.2 (d, $J_{C-P}$=9.3 Hz), 133.9 (d, $J_{C-P}$=10.6 Hz), 134.7 (d, $J_{C-P}$=3.1 Hz), 140.3.

Mass analysis as $C_{26}H_{22}N_2P$, Calculated: 393.1521 [M]$^+$, Found: 393.1525 [0.5 mDa].

Melting point: 265-266° C.

EXAMPLE 3

Synthesis of Compound 2

Compound (I) (340 mg, 2.29 mmol) obtained in the Reference Example 1 was dissolved in acetonitrile (3.5 mL) and aqueous solution of 47% hydrobromide (279 μL, 2.41 mmol) and triphenylphosphine (632 mg, 2.41 mmol) were added thereto under ice-cooling, followed by stirring for 10 hours under heating and reflux. After the reaction solution was concentrated under reduced pressure, precipitated crystal was suspended in acetonitrile (2 mL), followed by stirring for 3 hours at a room temperature. The crystal was collected by filtration and washed with acetonitrile (1 mL). Then, the obtained crystal was dried under reduced pressure to thereby yield Compound 2 (0.911 g, 1.92 mmol, 84%).

EXAMPLE 4

Synthesis of [(1H-indazol-3-yl)methyl]triphenylphosphonium iodide (Compound 3)

Compound (I) (1.00 g, 6.75 mmol) obtained in the Reference Example 1 was dissolved in propionitrile (20 mL) and aqueous solution of 57% hydroiodide (947 μL, 6.75 mmol) and triphenylphosphine (1.77 g, 6.75 mmol) were added thereto under ice-cooling, followed by stirring for 4.5 hours under heating and reflux. The reaction solution was concentrated under reduced pressure, and propionitrile (5 mL) was added to the residue, followed by stirring under heating and reflux for 1 hour. The mixture was stirred for 2 hours under ice-cooling, and then precipitated crystal was collected by filtration. The crystal was washed with propionitrile (5 mL) and was dried under reduced pressure to thereby yield Compound 3 (2.69 g, 5.16 mmol, 76%).

$^1$H-NMR (DMSO-$d_6$, ppm) δ 5.61 (2H, d, J=15.2 Hz), 7.00 (1H, t, J=ca. 8 Hz), 7.31 (1H, t, J=ca. 8 Hz), 7.45 (1H, d, J=8.4 Hz), 7.60 (1H, d, J=8.4 Hz), 7.67-7.88 (15H, m), 13.13 (1H, br).

$^{13}$C-NMR (DMSO-$d_6$, ppm) δ 20.9 (d, $J_{C-P}$=51.6 Hz), 110.2, 118.8 (d, $J_{C-P}$=86.4 Hz), 119.6, 120.3, 122.5 (d, $J_{C-P}$=5.6 Hz), 126.5, 129.8 (d, $J_{C-P}$=12.4 Hz), 133.2 (d, $J_{C-P}$=8.7 Hz), 133.8 (d, $J_{C-P}$=10.6 Hz), 134.7 (d, $J_{C-P}$=3.1 Hz), 140.3.

Mass analysis as $C_{26}H_{22}N_2P$, Calculated: 393.1521 [M]$^+$, Found: 393.1519 [−0.2 mDa].

Melting Point: 206-207° C.

EXAMPLE 5

Synthesis of [(1H-indazol-3-yl)methyl]triphenylphosphonium methanesulfonate (Compound 4)

Compound (I) (100 mg, 0.675 mmol) obtained in the Reference Example 1 was dissolved in propionitrile (2 mL) and methanesulfonic acid (51.6 μL, 0.709 mmol) and triphenylphosphine (186 mg, 0.709 mmol) were added thereto under ice-cooling, followed by stirring for 10 hours under heating and reflux. The reaction solution was concentrated under reduced pressure, and propionitrile (1 mL) was added to the residue, followed by stirring under ice-cooling for 2 hours. The precipitated crystal was collected by filtration and washed with propionitrile (0.5 mL). The obtained crystal was dried under reduced pressure to thereby yield Compound 4 (287 mg, 0.586 mmol, 87%).

$^1$H-NMR (DMSO-$d_6$, ppm) δ 2.36 (3H, s), 5.60 (2H, d, J=15.4 Hz), 6.99 (1H, t, J=ca. 8 Hz), 7.30 (1H, t, J=ca. 8 Hz), 7.46 (1H, d, J=8.4 Hz), 7.59 (1H, d, J=8.4 Hz), 7.66-7.87 (15H, m), 13.17 (1H, br).

$^{13}$C-NMR (DMSO-$d_6$, ppm) δ 20.8 (d, $J_{C-P}$=52.2 Hz), 39.7, 110.3, 118.9 (d, $J_{C-P}$=86.4 Hz), 119.6, 120.3, 122.6 (d, $J_{C-P}$=6.2 Hz), 126.5, 129.8 (d, $J_{C-P}$=12.4 Hz), 133.2 (d, $J_{C-P}$=9.3 Hz), 133.9 (d, $J_{C-P}$=10.6 Hz), 134.7 (d, $J_{C-P}$=53.1 Hz), 140.3.

Mass analysis as $C_{26}H_{22}N_2P$, Calculated: 393.1521 [M]$^+$, Found: 393.1525 [0.4 mDa].

Melting Point: 210-211° C.

EXAMPLE 6

Synthesis of [(1H-indazol-3-yl)methyl]triphenylphosphonium p-toluenesulfonate (Compound 5)

Compound (I) (100 mg, 0.675 mmol) obtained in the Reference Example 1 was dissolved in propionitrile (2 mL) and p-toluenesulfonic acid monohydrate (135 mg, 0.709 mmol) and triphenylphosphine (186 mg, 0.709 mmol) were added thereto under ice-cooling, followed by stirring for 10 hours under heating and reflux. The reaction solution was concentrated under reduced pressure, and propionitrile (1 mL) was added to the residue, followed by stirring under ice-cooling for 2 hours. The precipitated crystal was collected by filtration and washed with propionitrile (0.5 mL). The obtained crystal was dried under reduced pressure to thereby yield Compound 5 (284 mg, 0.503 mmol, 75%).

$^1$H-NMR (DMSO-$d_6$, ppm) δ 2.27 (3H, s), 5.59 (2H, d, $J_{H-C-P}$=15.2 Hz), 6.99 (1H, t, J=ca. 8 Hz), 7.10 (2H, d, J=8.0 Hz), 7.30 (1H, t, J=ca. 8 Hz), 7.45 (1H, d, J=8.4 Hz), 7.49 (2H, d, J=8.0 Hz) 7.58 (1H, d, J=8.4 Hz), 7.69-7.86 (15H, m), 13.17 (1H, br).

$^{13}$C-NMR (DMSO-$d_6$, ppm) δ 20.7, 20.8 (d, $J_{C-P}$=52.2 Hz), 110.2, 118.8 (d, $J_{C-P}$=86.4 Hz), 119.6, 120.3, 122.5 (d, $J_{C-P}$=6.2 Hz), 125.4, 126.5, 128.0, 129.8 (d, $J_{C-P}$=12.4 Hz), 133.2 (d, $J_{C-P}$=9.3 Hz), 133.9 (d, $J_{C-P}$=10.6 Hz), 134.7 (d, $J_{C-P}$=3.1 Hz), 137.5, 140.33, 145.8.

Mass analysis as $C_{26}H_{22}N_2P$, Calculated: 393.1521 [M]$^+$, Found: 393.1511 [−0.9 mDa].

Melting Point: 209-210° C.

EXAMPLE 7

Synthesis of [(1H-indazol-3-yl)methyl]triphenylphosphonium trifluoromethanesulfonate (Compound 6)

Compound (I) (100 mg, 0.675 mmol) obtained in the Reference Example 1 was dissolved in propionitrile (2 mL) and trifluoromethanesulfonic acid (62.7 μL, 0.709 mmol) and triphenylphosphine (186 mg, 0.709 mmol) were added thereto under ice-cooling, followed by stirring for 4 hours under heating and reflux. The reaction solution was concentrated under reduced pressure, and ethyl acetate (1 mL) was added to the residue, followed by stirring under ice-cooling for 2 hours. The precipitated crystal was collected by filtration and was washed with ethyl acetate (0.5 mL). The obtained crystal was dried under reduced pressure to thereby yield Compound 6 (269 mg, 0.496 mmol, 74%).

$^1$H-NMR (DMSO-$d_6$, ppm) δ 5.59 (2H, d, J=15.2 Hz), 7.00 (1H, t, J=ca. 8 Hz), 7.30 (1H, t, J=ca. 8 Hz), 7.44 (1H, d, J=8.4 Hz), 7.58 (1H, d, J=8.4 Hz), 7.66-7.86 (15H, m), 13.17 (1H, br).

$^{13}$C-NMR (DMSO-$d_6$, ppm) δ 20.8 (d, $J_{C-P}$=51.6 Hz), 110.2, 118.8 (d, $J_{C-P}$=87.0 Hz), 119.6, 120.4, 120.7 (q, $J_{C-F}$=322.6 Hz), 122.6 (d, $J_{C-P}$=5.6 Hz), 126.5, 129.8 (d, $J_{C-P}$=12.4 Hz), 133.2 (d, $J_{C-P}$=9.3 Hz), 133.8 (d, $J_{C-P}$=10.6 Hz), 134.7 (d, $J_{C-P}$=3.1 Hz), 140.3.

Mass analysis as $C_{26}H_{22}N_2P$, Calculated: 393.1521 [M]$^+$, Found: 393.1511 [−0.9 mDa].

Melting Point: 152-153° C.

EXAMPLE 8

Synthesis of [(1H-indazol-3-yl)methyl]triphenylphosphonium trifluoroacetate (Compound 7)

Compound (I) (150 mg, 1.01 mmol) obtained in the Reference Example 1 was dissolved in propionitrile (1.5 mL), then trifluoroacetic acid (81.9 μL, 1.06 mmol) and triphenylphosphine (279 mg, 1.06 mmol) were added thereto under ice-cooling, followed by stirring for 24 hours under heating and reflux. After the reaction, methanol was added and production rate of Compound 7 was calculated by high-performance liquid chromatography (HPLC) analysis (production rate 59%).

HPLC Condition
  Apparatus: Manufactured by Hitachi, Ltd.
  Column: YMC-Pack ODS AM-302, 150×4.6 mm (manufactured by YMC)
  Mobile phase: methanol/phosphate buffer=40/60 (phosphate buffer was prepared by dissolving 20 mmol of $KH_2PO_4$ and 20 mmol of $K_2HPO_4$ to 1 L of water)
  Temperature: 35° C.
  Flow rate: 1.0 mL/minute
  Detection: UV (254 nm)
  Measuring time: 30 minutes $^1$H-NMR (DMSO-$d_6$, ppm) δ 5.65 (2H, d, J=15.2 Hz), 7.00 (1H, t, J=ca. 8 Hz), 7.29 (1H, t, J=ca. 8 Hz), 7.48 (1H, d, J=8.4 Hz), 7.63 (1H, d, J=8.4 Hz), 7.71-7.86 (15H, m), 13.36 (1H, br).

$^{13}$C-NMR (DMSO-$d_6$, ppm) δ 20.9 (d, $J_{C-P}$=51.0 Hz), 110.3, 116.9 (q, $J_{C-F}$=297.72 Hz), 118.9 (d, $J_{C-P}$=86.4 Hz), 119.6, 120.3, 122.6 (d, $J_{C-P}$=5.6 Hz), 126.4, 129.8 (d, $J_{C-P}$=12.4 Hz), 133.2 (d, $J_{C-P}$=9.3 Hz), 133.9 (d, $J_{C-P}$=10.6 Hz), 134.7 (d, $J_{C-P}$=2.5 Hz), 140.4, 158.1 (q, $J_{C-P}$=32.1 Hz).

REFERENCE EXAMPLE 1

Synthesis of (1H-indazol-3-yl)methanol [Compound (I)]

Commercially available indazol-3-carboxylic acid (500 mg, 3.08 mmol) was dissolved in tetrahydrofuran (THF) (10 mL) and sodium bis(2-methoxyethoxy)aluminum hydride (70% toluene solution, 1.78 g, 6.17 mmol) was added thereto under ice-cooling, under argon atmosphere, followed by stirring for 2 hours under heating and reflux. Sodium bis(2-methoxyethoxy)aluminum hydride (70% toluene solution, 2.67 g, 9.25 mmol) was further added to the mixture under ice-cooling and the mixture was stirred for 2 hours under heating and reflux. Under ice-cooling, 2 mol/L sodium hydroxide solution (10 mL) was added, and the mixture was stirred for 15 minutes at a room temperature. The organic layer was separated and the aqueous layer was extracted with THF (5 mL, 3 times). The organic layer was collected, and washed with saturated brine. The aqueous layer was extracted with ethyl acetate (5 mL, 2 times), all organic layers were collected and dried over anhydrous magnesium sulfate followed by concentration under reduced pressure. The residue was recrystallized by toluene/THF (10:1) (5 mL) and the precipitated crystal was collected by filtration, followed by washing with torulene/THF (10:1) (1 mL). The obtained crystal was dried under reduced pressure to thereby yield Compound (I) (349 mg, 2.36 mmol, 77%).

$^1$H-NMR (DMSO-$d_6$, ppm) δ 4.80 (2H, d, J=5.5 Hz), 5.19 (1H, br), 7.09 (1H, t, J=ca. 8 Hz), 7.33 (1H, t, J=ca. 8 Hz), 7.48 (1H, d, J=8.4 Hz), 7.85 (1H, d, J=8.4 Hz).

$^{13}$C-NMR (DMSO-$d_6$, ppm) δ 56.7, 109.9, 119.6, 120.5, 121.4, 125.8, 140.9, 145.5.

Mass analysis as $C_8H_9N_2O$, Calculated: 149.0715 [M+H]$^+$,

Found: 149.0710 [−0.5 mDa].

Melting Point: 142-143° C.

REFERENCE EXAMPLE 2

Synthesis of methyl (E)-4-[2-(1H-indazol-3-yl)vinyl]benzoate using Compound 1

Compound 1 (500 mg, 1.17 mmol) was dissolved in methanol (3 mL) and 1,8-diazabicyclo[5.4.0]undece-7-en (DBU) (262 μL, 1.69 mmol) and methyl 4-formylbenzoate (211 mg, 1.28 mmol) were added thereto under ice-cooling, followed by stirring for 7 hours at a room temperature. The reaction solution was stirred for 2.5 hours under ice-cooling, and precipitated crystal was collected by filtration, followed by washing with methanol (1.5 mL). The obtained crystal was dried under reduced pressure to thereby yield methyl (E)-4-[2-(1H-indazol-3-yl)vinyl]benzoate (156 mg, 0.562 mmol, 48%).

$^1$H-NMR (DMSO-$d_6$, ppm) δ 3.87 (3H, s), 7.24 (1H, m), 7.42 (1H, m), 7.58 (1H, d, J=8.3 Hz), 7.60 (1H, d, J=16.7 Hz), 7.74 (1H, d, J=16.7 Hz), 7.87 (2H, d, J=8.4 Hz), 7.98 (2H, d, J=8.4 Hz), 8.24 (1H, d, J=8.0 Hz), 13.30 (1H, br s).

Mass analysis as $C_{17}H_{15}N_2O_2$, Calculated: 279.1134 [M+H]$^+$,

Found: 279.1130 [−0.4 mDa].

REFERENCE EXAMPLE 3

Synthesis of methyl (E)-4-[2-(1H-indazol-3-yl)vinyl]methyl using Compound 2

Compound 2 (4.00 g, 8.50 mmol) was dissolved in methanol (30 mL) and DBU (1.90 mL, 12.7 mmol) and methyl 4-formylbenzoate (1.39 g, 8.45 mmol) were added thereto under ice-cooling, followed by stirring for 3.5 hours at a room temperature. The reaction solution was stirred for 2.5 hours under ice-cooling, and precipitated crystal was collected by filtration, followed by washing with methanol (10 mL). The obtained crystal was dried under reduced pressure to thereby yield methyl (E)-4-[2-(1H-indazol-3-yl)vinyl]benzoate (1.35 g, 4.86 mmol, 57%).

REFERENCE EXAMPLE 4

Synthesis of methyl (E)-4-[2-(1H-indazol-3-yl)vinyl]benzoate using Compound 3

Compound 3 (101 mg, 0.194 mmol) was dissolved in methanol (1 mL) and DBU (44.0 μL, 0.467 mmol) and methyl 4-formylbenzoate (35.1 mg, 0.233 mmol) were added thereto under ice-cooling, followed by stirring for 5 hours at a room temperature. After the reaction, methanol was added and production rate of methyl (E)-4-[2-(1H-indazol-3-yl)vinyl]benzoate was calculated by HPLC analysis (production rate 69%). A measuring condition of HPLC is as follows.

HPLC Condition
  Apparatus: Manufactured by Hitachi, Ltd.
  Column: Cadenza CD-C-18, 75 mm×4.6 mm (manufactured by Intact)
  Mobile phase: methanol/phosphate buffer=from 45/55 (0 to 25 minutes) to 60/40 (30 to 55 minutes)(phosphate buffer was prepared by dissolving 20 mmol of $KH_2PO_4$ and 20 mmol of $K_2HPO_4$ to 1 L of water)
  Temperature: 35° C.
  Flow rate: 1.0 mL/minute
  Detection: UV (254 nm)
  Measuring time: 55 minutes

REFERENCE EXAMPLE 5

Synthesis of methyl (E)-4-[2-(1H-indazol-3-yl)vinyl]benzoate using Compound 4

Compound 4 (54.0 mg, 0.111 mmol) was dissolved in methanol (1 mL) and DBU (25.0 μL, 0.265 mmol) and methyl 4-formylbenzoate (20.0 mg, 0.133 mmol) were added thereto under ice-cooling, followed by stirring for 5 hours at a room temperature. After the reaction, methanol was added and production rate of methyl (E)-4-[2-(1H-indazol-3-yl)vinyl]benzoate was calculated by HPLC analysis in a similar manner to Reference Example 4 (production rate 59%).

REFERENCE EXAMPLE 6

Synthesis of methyl (E)-4-[2-(1H-indazol-3-yl)vinyl]benzoate using Compound 5

Compound 5 (50.7 mg, 89.7 μmol) was dissolved in methanol (1 mL) and DBU (20.1 μL, 0.215 mmol) and methyl 4-formylbenzoate (16.2 mg, 0.108 mmol) were added thereto, under ice-cooling, followed by stirring for 5 hours at a room temperature. After the reaction, methanol was added and production rate of methyl (E)-4-[2-(1H-indazol-3-yl)vinyl]benzoate was calculated by HPLC analysis in a similar manner to Reference Example 4 (production rate 67%).

REFERENCE EXAMPLE 7

Synthesis of methyl (E)-4-[2-(1H-indazol-3-yl)vinyl]benzoate using Compound 6

Compound 6 (50.7 mg, 93.5 μmol) was dissolved in methanol (1 mL) and DBU (21.0 μL, 0.224 mmol) and methyl 4-formylbenzoate (16.9 mg, 0.112 mmol) were added thereto, under ice-cooling, followed by stirring for 5 hours at a room temperature. After the reaction, methanol was added and production rate of methyl (E)-4-[2-(1H-indazol-3-yl)vinyl]benzoate was calculated by HPLC analysis in a similar manner to Reference Example 4 (production rate 67%).

INDUSTRIAL APPLICABILITY

The present invention provides a method for producing an indazol-3-ylmethyl phosphonium salt or a salt thereof useful as a synthetic intermediate of an indazol derivative having antitumor activity, protein kinase inhibitory activity or the like, etc.

The invention claimed is:

1. A method for producing an indazol-3-ylmethyl phosphonium salt represented by Formula (IV):

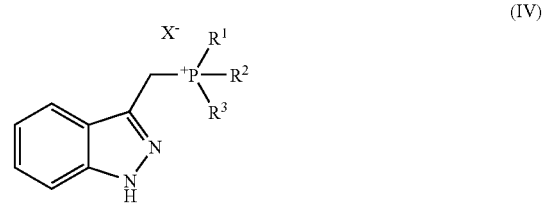

(IV)

[wherein, X represents halogen, $ONO_2$, $OSO_3H$, $OSO_2R^a$ (wherein $R^a$ represents substituted or unsubstituted lower alkyl, substituted or unsubstituted aryl, or a substituted or unsubstituted aromatic heterocyclic group), or $OC(=O)R^b$ (wherein $R^b$ has the same meaning as the above $R^a$), and $R^1$, $R^2$ and $R^3$ may be the same or different and each represents substituted or unsubstituted aryl or a substituted or unsubstituted aromatic heterocyclic group] or a salt thereof, which comprises reacting a compound represented by Formula (I):

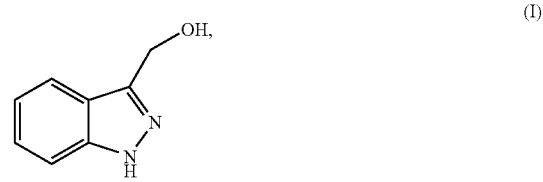

(I)

a compound represented by Formula (II):

H—X    (II), and a compound represented by Formula (III):

(III)

2. The method for producing an indazol-3-ylmethyl phosphonium salt or a salt thereof according to claim 1, wherein $R^1$, $R^2$ and $R^3$ may be the same or different and each represents substituted or unsubstituted aryl.

3. The method for producing an indazol-3-ylmethyl phosphonium salt or a salt thereof according to claim 1, wherein $R^1$, $R^2$ and $R^3$ are phenyl.

4. The method for producing an indazol-3-ylmethyl phosphonium salt or a salt thereof according to any of claims 1 to 3, wherein X is halogen.

5. The method for producing an indazol-3-ylmethyl phosphonium salt or a salt thereof according to any of claims 1 to 3, wherein X is $ONO_2$, $OSO_3H$, $OSO_2R^a$, or $OC(=O)R^b$.

6. The method for producing an indazol-3-ylmethyl phosphonium salt or a salt thereof according to any of claims 1 to 3, wherein X is $OSO_2R^a$.

7. The method for producing an indazol-3-ylmethyl phosphonium salt or a salt thereof according to any of claims 1 to 3, wherein X is $OC(=O)R^b$.

8. A method for producing an indazole derivative represented by Formula (V):

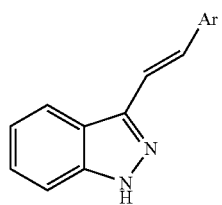

(V)

(wherein, Ar represents substituted or unsubstituted aryl, or a substituted or unsubstituted heterocyclic group) or a salt thereof, which comprises a step of reacting a compound represented by Formula (I):

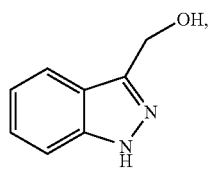

(I)

a compound represented by Formula (II):

H—X        (II)

(wherein X represents halogen, $ONO_2$, $OSO_3H$, $OSO_2R^a$ (wherein $R^a$ represents substituted or unsubstituted lower alkyl, substituted or unsubstituted aryl, or a substituted or unsubstituted aromatic heterocyclic group), or $OC(=O)R^b$ (wherein $R^b$ has the same meaning as the above $R^a$)) and a compound represented by Formula (III):

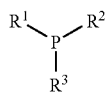

(III)

(wherein $R^1$, $R^2$ and $R^3$ may be the same or different and each represents substituted or unsubstituted aryl or a substituted or unsubstituted aromatic heterocyclic group) to obtain an indazol-3-ylmethyl phosphonium salt represented by Formula (IV):

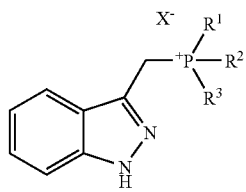

(IV)

or a salt thereof.

9. The method for producing an indazole derivative or a salt thereof according to claim 8, wherein Ar is substituted or unsubstituted aryl.

10. The method for producing an indazole derivative or a salt thereof according to claim 8, wherein Ar is substituted or unsubstituted phenyl.

11. The method for producing an indazole derivative or a salt thereof according to claim 8, wherein Ar is a substituted or unsubstituted aromatic heterocyclic group.

* * * * *